United States Patent
Kim

(10) Patent No.: US 10,444,307 B2
(45) Date of Patent: Oct. 15, 2019

(54) SURFACE COIL FOR MAGNETIC RESONANCE IMAGING SYSTEM AND MAGNETIC RESONANCE IMAGING SYSTEM INCLUDING SAME

(71) Applicant: SAMSUNG ELECTRONICS CO., LTD., Suwon-si (KR)

(72) Inventor: Kyoung Nam Kim, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 101 days.

(21) Appl. No.: 15/529,307

(22) PCT Filed: Nov. 20, 2015

(86) PCT No.: PCT/KR2015/012567
§ 371 (c)(1),
(2) Date: May 24, 2017

(87) PCT Pub. No.: WO2016/085207
PCT Pub. Date: Jun. 2, 2016

(65) Prior Publication Data
US 2017/0261570 A1  Sep. 14, 2017

(30) Foreign Application Priority Data
Nov. 25, 2014  (KR) .................. 10-2014-0165401

(51) Int. Cl.
*G01R 33/3415* (2006.01)
*A61B 5/055* (2006.01)
*G01R 33/36* (2006.01)

(52) U.S. Cl.
CPC .......... *G01R 33/3415* (2013.01); *A61B 5/055* (2013.01); *G01R 33/36* (2013.01)

(58) Field of Classification Search
CPC .............. G01R 33/5608; G01R 33/543; G01R 33/3815; G01R 33/3804; G01R 33/385
(Continued)

(56) References Cited

U.S. PATENT DOCUMENTS 4,780,677 A * 10/1988 Nissenson ............ G01R 33/343
　　　　　　　　　　　　　　　　　　　324/322
5,144,243 A *  9/1992 Nakabayashi ..... G01R 33/3415
　　　　　　　　　　　　　　　　　　　324/318
(Continued)

FOREIGN PATENT DOCUMENTS

JP　　10-024025 A　　1/1998
JP　　2008-086837 A　　4/2008
(Continued)

OTHER PUBLICATIONS

International Search Report dated Mar. 25, 2016 in International Application No. PCT/KR2015/012567.

*Primary Examiner* — Christopher P McAndrew
(74) *Attorney, Agent, or Firm* — NSIP Law

(57) ABSTRACT

A surface coil for a magnetic resonance imaging system includes a first plane coil placed on a first plane. A first curved surface coil is disposed symmetrically to the first place coil and disposed on one curved surface. The first plane coil is disposed tangentially to the first curved surface coil, wherein the first plane coil and the first curved surface coil are electrically connected to each other through at least two surface portions.

20 Claims, 17 Drawing Sheets

(58) Field of Classification Search
USPC ........................................................ 324/322
See application file for complete search history.

(56) References Cited

U.S. PATENT DOCUMENTS

| | | | |
|---|---|---|---|
| 5,433,717 A * | 7/1995 | Rubinsky | ............... A61B 18/02 |
| | | | 600/411 |
| 5,804,969 A | 9/1998 | Lian et al. | |
| 5,939,883 A * | 8/1999 | Green | .............. G01R 33/34061 |
| | | | 324/318 |
| 6,081,120 A | 6/2000 | Shen | |
| 6,097,186 A | 8/2000 | Nabetani | |
| 6,163,240 A * | 12/2000 | Zuk | .................... G01R 33/3806 |
| | | | 324/318 |
| 6,348,794 B1 | 2/2002 | Nabetani et al. | |
| 6,700,378 B2 * | 3/2004 | Sato | .................... G01R 33/381 |
| | | | 324/318 |
| 7,446,533 B2 | 11/2008 | Ogino | |
| 7,570,059 B2 | 8/2009 | Greim et al. | |
| 7,898,255 B2 | 3/2011 | Ochi et al. | |
| 2003/0102866 A1 * | 6/2003 | Katscher | .............. G01R 33/446 |
| | | | 324/318 |
| 2012/0262173 A1 * | 10/2012 | Soutome | .......... G01R 33/34076 |
| | | | 324/309 |
| 2014/0167758 A1 | 6/2014 | Sambandamurthy | |
| 2016/0131725 A1 | 5/2016 | Sambandamurthy | |

FOREIGN PATENT DOCUMENTS

| | | |
|---|---|---|
| JP | 2011-056164 A | 3/2011 |
| JP | 4749417 B2 | 8/2011 |
| JP | 2013-106862 A | 6/2013 |
| JP | 2013-530019 A | 7/2013 |
| KR | 10-1999-0088363 A | 7/1999 |
| KR | 10-2007-0041351 A | 4/2007 |
| KR | 1270081 B1 | 5/2013 |
| WO | WO 2007/081805 A2 | 7/2007 |

* cited by examiner (A)

(B)

(C)

(A)

(B)

(C)

SURFACE COIL FOR MAGNETIC RESONANCE IMAGING SYSTEM AND MAGNETIC RESONANCE IMAGING SYSTEM INCLUDING SAME

CROSS REFERENCE TO RELATED APPLICATIONS

This application is a U.S. national stage application of International Application No. PCT/KR2015/012567, filed on Nov. 20, 2015, which claims the benefit of Korean Patent Application No. 10-2014-0165401, filed on Nov. 25, 2014, in the Korean Intellectual Property Office, the entire disclosures of which are incorporated herein by reference for all purposes.

BACKGROUND

1. Field

This disclosure relates to a surface coil for a magnetic resonance imaging system and a magnetic resonance imaging system including the same.

2. Description of Related Art

A magnetic resonance image (MRI) indicates a technology of putting an examinee in a huge magnetic container generating a magnetic field, resonating a hydrogen atom nucleus included in the examinee by generating a radio frequency, measuring a difference of signals from each organ of the examinee, reconstituting them through a computer, and realizing them as an image. The image is obtained by applying a radio frequency (RF) pulse to the examinee in a device made of a magnet, receiving the signals emitted like an echo from the examinee, and converting the signals into digital information.

A magnetic resonance imaging system uses various coils such as a gradient coil, a body coil, a surface coil, and the like. The surface coil is disposed closest to the examinee, and performs a function of receiving or transmitting high frequency signals. In general, a surface coil mainly includes a single-layer planar (SLP) coil and a single-layer circular (SLC) coil.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Performance (uniformity and sensitivity of a magnetic field and the like) of the surface coil may vary depending on a physical size, a housing shape, a RF shield, and the like, and in addition, a region where the magnetic field (a B1 field) generated by the surface coil is formed may be changed by adjusting a depth pulse. The B1 field is a region corresponding to a radius of the coil (when an examinee noise is prominent) or 1.5 times as large as the radius of the coil (when a RF coil noise is prominent). Accordingly, the coil size may be determined depending on how far a region of interest (ROI) is apart from the surface coil.

In order to improve sensitivity or a permeability depth of the B1 field, a single-layer planar (SLP) coil may be transformed into a single-layer circular (SLC) coil, but it is still difficult to improve a signal-to-noise ratio (SNR) of a magnetic resonance image. A mere 5% improvement of the signal-to-noise ratio (SNR) of the magnetic resonance may remarkably improve clarity of the magnetic resonance image. Accordingly, a surface coil capable of improving the signal-to-noise ratio of a magnetic resonance image is provided.

In one general aspect, a surface coil for a magnetic resonance imaging system according to an embodiment includes a first plane coil placed on a first plane. A first curved surface coil is disposed symmetrically to the first plane coil and disposed on one curved surface. The first plane coil is disposed tangentially to the first curved surface coil, wherein the first plane coil and the first curved surface coil are electrically connected to each other through at least two surface portions.

The magnetic resonance imaging system may further include at least one first capacitor connected to any one or any combination of the first plane coil and the first curved surface coil, and at least one of the at least one first capacitor may be disposed in a connecting region where the first curved surface coil is connected to the first plane coil. The first plane coil is severed to have both ends at the connecting region, the first curved surface coil is also severed to have both ends at the connecting region, and the capacitor disposed on the connecting region may be connected between both of the severed ends of the first plane and curved surface coils.

The first plane coil has a quadrilateral shape, and the first curved surface coil has a parabolic cylinder shape. The first plane coil is disposed tangentially to the first curved surface coil, the first plane coil and the first curved surface coil are respectively severed to have both ends at the tangent, and both of the severed ends of the first plane coil may be respectively connected to both of the severed ends of the curved surface coil. The magnetic resonance imaging system may further include a first capacitor connected between both of the severed ends of the first plane and curved surface coils. A second capacitor respectively inserted in two facing straight sides of the first curved surface coil may be further included.

The surface coil may further include a second plane coil disposed on a second plane, and a second curved surface coil having a parabolic cylinder shape and symmetrically disposed with the second plane coil and disposed on one curved surface, and the second plane coil disposed tangentially to the second curved surface coil, wherein the second plane coil and the second curved surface coil are electrically connected to each other through at least two surface portions.

The first plane coil and the second plane coil are disposed to face each other in parallel, and the first curved surface coil and the second curved surface coil may be disposed around a cylindrical axis.

At least one first capacitor connected to any one or any combination of the first plane coil and the first curved surface coil and at least one second capacitor connected to any one or any combination of the second plane coil and the second curved surface coil may be further included.

The surface coil may further include a third plane coil disposed on a third plane, and a third curved surface coil having a parabolic cylinder shape and disposed symmetrically to the third plane coil, and the third plane coil disposed tangentially to the third curved surface coil, wherein the third plane coil and the third curved surface coil are electrically connected to each other through at least two surface portions.

The surface coil may further include a fourth plane coil disposed on a fourth plane, and a fourth curved surface coil having a parabolic cylinder shape and disposed symmetrically to the fourth plane coil, and the fourth plane coil disposed tangentially to the fourth curved surface coil, wherein the fourth plane coil and the fourth curved surface coil are electrically connected to each other through at least two surface portions. The third plane coil and the fourth plane coil are disposed to face each other in parallel, and the third curved surface coil and the fourth curved surface coil may be disposed around the cylindrical axis. The first plane coil and the third plane are perpendicular each to the other.

At least one first capacitor connected to either one of the first plane coil and the first curved surface coil, at least one second capacitor connected to either one of the second plane coil and the second curved surface coil, at least one third capacitor connected to either one of the third plane coil and the third curved surface coil, and at least one fourth capacitor connected to any one or any combination of the fourth plane coil and the fourth curved surface coil may be further included.

A magnetic resonance imaging system according to an embodiment includes a first plane coil disposed on one plane, and a first curved surface coil disposed symmetrically to the first plane coil and disposed on one curved surface, wherein the first plane coil and the first curved surface coil are electrically connected to each other in at least two parts of the surface coil.

According to an embodiment, quality of a magnetic resonance image may be enhanced by improving a signal-to-noise ratio (SNR) of a magnetic resonance imaging system.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
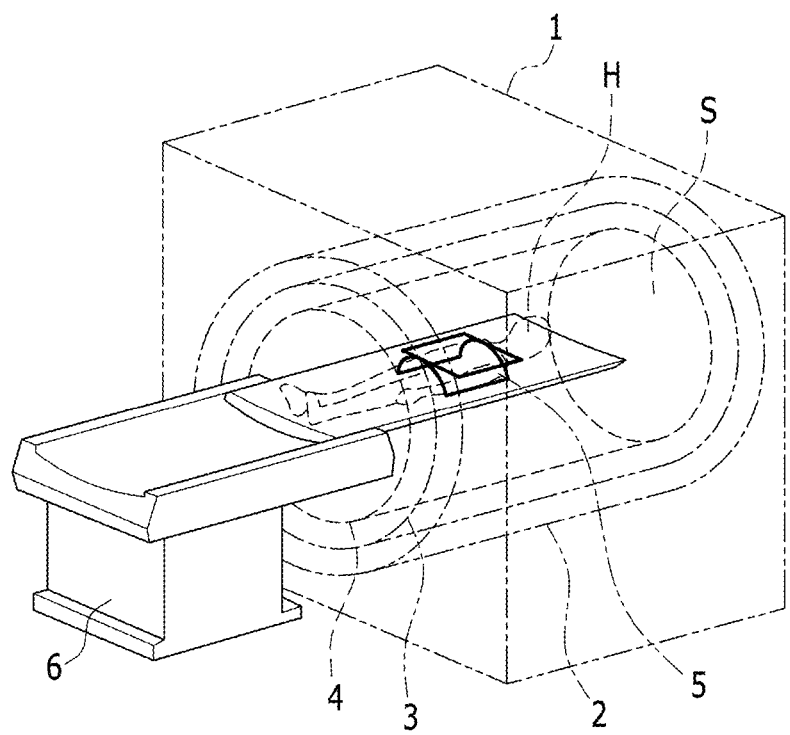
FIG. 1 is a perspective view showing a magnetic resonance imaging system according to an embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Figure 2:
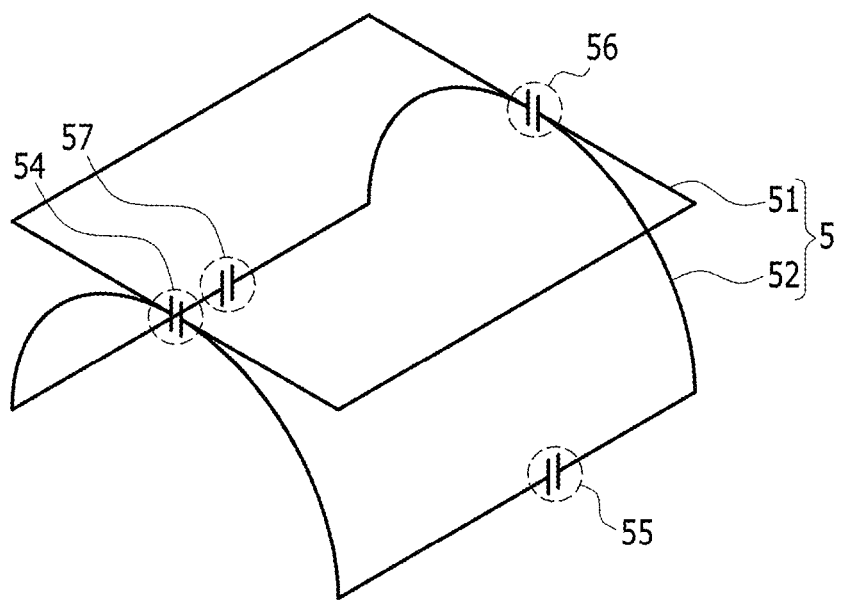
FIG. 2 is a perspective view showing a surface coil for a magnetic resonance imaging system according to an embodiment.

FIG. 1 is a perspective view showing a magnetic resonance imaging system according to an embodiment, and FIG. 2 is a perspective view of a surface coil for a magnetic resonance imaging system according to an embodiment.

Referring to FIG. 1, a magnetic resonance imaging system 1 according to an embodiment includes a main magnetic field-generating magnet 2, a gradient coil 3 cylindrically mounted inside the main magnetic field-generating magnet 2, a body coil 4 cylindrically mounted inside the gradient coil 3, a surface coil 5 mounted closely to an examinee (H) on a space (S) formed inside the body coil 4, a table device 6 loading and moving the examinee (H) and the like, and the like. The main magnetic field-generating magnet 2 forms a main magnetic field in the space (S) where an examinee (H) is placed, and the gradient coil 3 includes three gradient coils having each of X, Y, and Z axes and wound around an internal cylinder as a device obtaining information by temporarily changing intensity of the main magnetic field depending on a position, and a signal amplifier flowing a current to the gradient coils. The body coil 4 transmits a radio frequency (RF) signal, and may receive the RF signal. The surface coil 5 transmits and receives the RF signal. In an alternative embodiment, the surface coil 5 only receives the RF signal.

Referring to FIG. 2, the surface coil 5 for a magnetic resonance imaging system according to an embodiment includes a plane coil unit 51 and a curved surface coil unit 52, two capacitors 54 and 56 inserted on a contact point of the plane coil unit 51 and the curved surface coil unit 52, and two capacitors 55 and 57 inserted in a straight line of the curved surface coil unit 52.

The plane coil unit 51 has a rectangular shape and is severed at a place where the two capacitors 54 and 56 are inserted.

The curved surface coil unit 52 includes two circular arc parts having a circular arc shape, and two straight line parts. The two circular arc parts are disposed to face each other in parallel, and respective ends of the two circular arc parts are connected to two straight line parts. In other words, the curved surface coil unit 52 has a circular arc shape of which two facing sides of a rectangle are curved. The curved surface coil unit 52 is severed at four places where four capacitors are inserted.

The plane coil unit 51 is disposed on a plane substantially parallel to another plane where the two straight lines of the curved surface coil unit 52 are disposed and closest to the curved surface coil unit 52 at the centers of the two circular arc parts. The curved surface coil unit 52 is projected on the plane where the plane coil unit 51 is disposed so that a projected shadow of the curved surface coil unit 52 sheds inside the plane coil unit 51 or includes the plane coil unit 51. The projected shadow of the curved surface coil unit 52 may be substantially congruent with the plane coil unit 51.

The plane coil unit 51 and the curved surface coil unit 52 are electrically connected each other at a place where the two capacitors 54 and 56 are inserted. Their connection may be made through two electrodes of the two capacitors 54 and 56 or through a separate wire.

In the present embodiment, the two capacitors 55 and 57 simultaneously connected to the plane coil unit 51 and the curved surface coil unit 52 and inserted in the straight line parts of the curved surface coil unit 52 are further included, in addition to the capacitors 54 and 56. The surface coil 5 forms a series resonance circuit (an LC series resonance circuit) of an inductor and a capacitor through the connection, and inductance (L) and capacitance (C) are adjusted according to a desired resonance frequency (an operation frequency of a magnetic resonance imaging system). In addition, a disposition position and the number of capacitors may be changed. For example, the capacitors 55 and 57 disposed in the straight line part of the curved surface coil unit 52 are omitted, or another capacitor is additionally disposed in the plane coil unit 51. In addition, the capacitors 54 and 56 may be omitted by connecting the plane coil unit 51 with the curved surface coil unit 52, and a capacitor may be additionally disposed in the plane coil unit 51. However, the capacitors 54 and 56 are disposed at a position simultaneously connected to the plane coil unit 51 and the curved surface coil unit 52 to improve efficiency of the capacitor disposition.

Performance of this surface coil 5 is illustrated.

Figure 3:
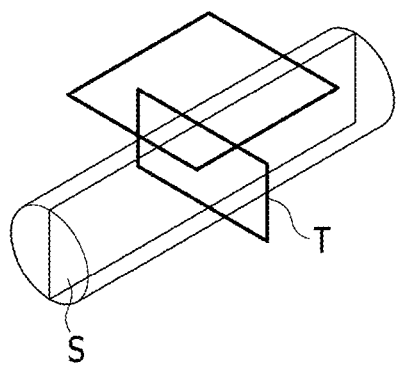
FIG. 3 shows perspective views of each state in which a single-layer planar coil (SLP), a single-layer circular coil (SLC), and a double layer coil (DLC) according to an embodiment are respectively mounted on a cylindrical examinee.
Figure 3:
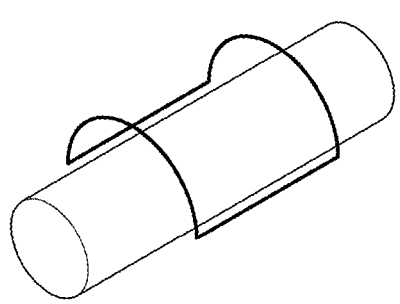
Figure 3:
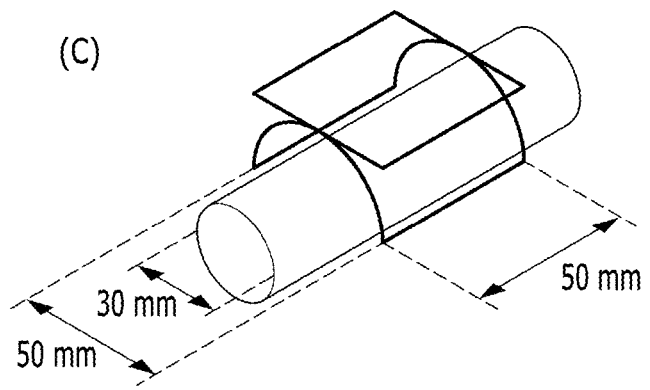
Figure 4:
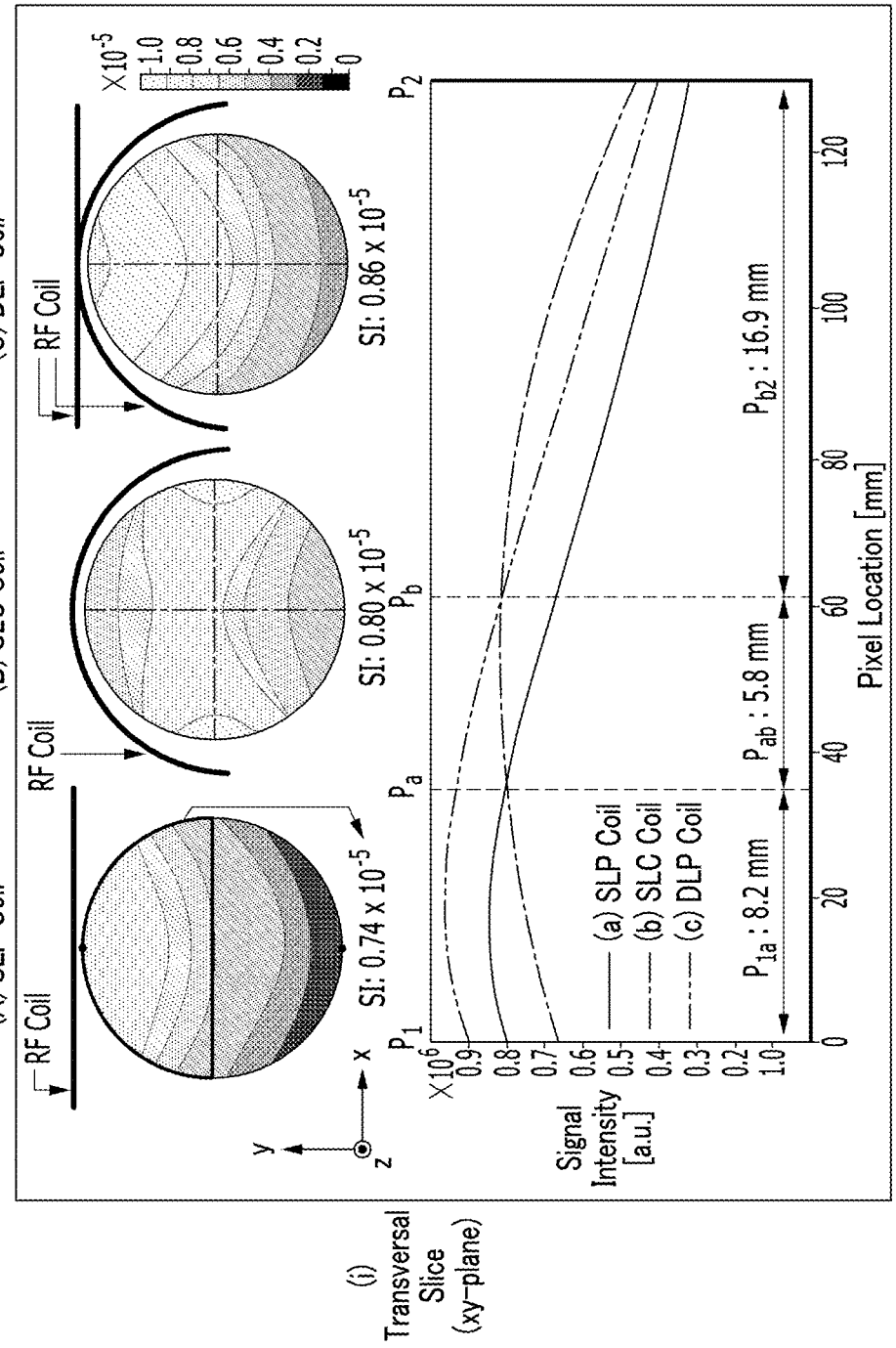
FIG. 4 is a graph showing a magnetic field measured along the T cross-section of the examinee on which the surface coils are mounted as shown in FIG. 3, and signal intensity depending on a position.
Figure 5:
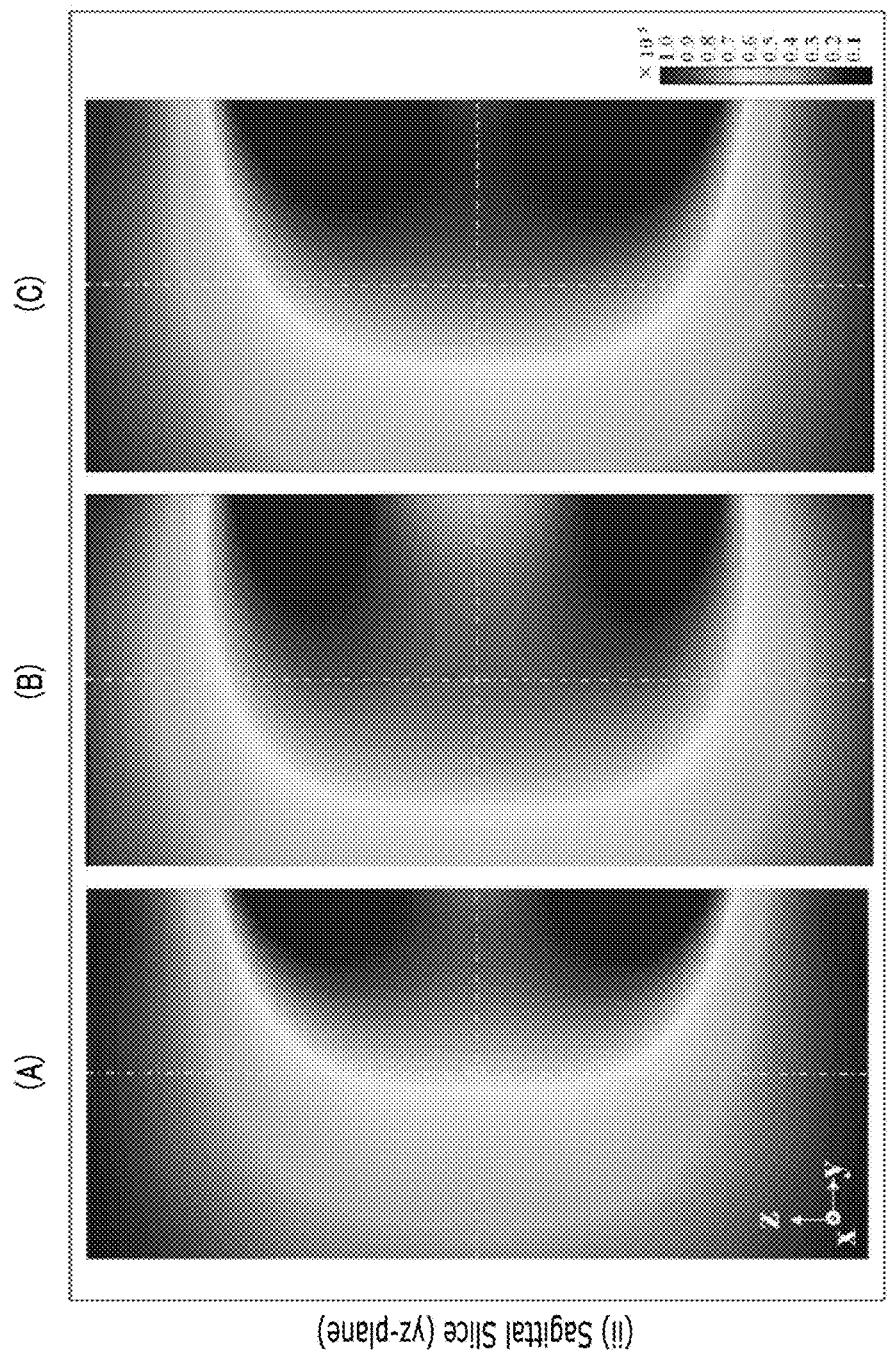
FIG. 5 is a graph showing a map of a magnetic field measured along the S cross-section of the examinee on which the surface coils are mounted as shown in FIG. 3.

FIG. 3 is perspective views showing each state in which a single-layer planar coil (SLP), a single-layer circular coil (SLC), and a double layer surface coil (DLC) according to an embodiment are respectively mounted on a cylindrical examinee, FIG. 4 shows a magnetic field map measured along a T cross-section of the examinee on which the surface coils are mounted, and signal intensity depending on a position as shown in FIG. 3, and FIG. 5 is a graph showing a magnetic field map measured along an S cross-section of the examinee on which the surface coils are mounted as shown in FIG. 3.

(A) of FIG. 3 shows that the single-layer planar coil (SLP) is mounted on the cylindrical examinee, (B) shows that the single-layer circular coil (SLC) is mounted on the cylindrical examinee, and (C) shows that the double layer surface coil (DLC) according to an embodiment is mounted on the cylindrical examinee. In (C), a size of the double layer surface coil (DLC) manufactured for a test is shown.

In the signal intensity graph of FIG. 4, a legend "(a) SLP Coil" indicates a case that the single-layer planar coil (SLP) is mounted on the cylindrical examinee, a legend "(b) SLC Coil" indicates a case that the single-layer circular coil (SLC) is mounted on the cylindrical examinee, and a legend "(c) DLC Coil" indicates a case that the double layer surface coil (DLC) according to an embodiment is mounted on the cylindrical examinee.

Referring to FIGS. 4 and 5, for the single-layer planar coil (SLP), a B1 field is strong at a position neighboring the coil, but the B1 field is sharply deteriorated farther from the coil. The single-layer circular coil (SLC) shows characteristics that the B1 field appears strong around the straight line parts where the capacitors are disposed. In other words, the single-layer circular coil (SLC) shows strong signal intensity in the center of the examinee. The double layer surface coil (DLC) according to an embodiment forms a strong B1 field at a position neighboring the surface coil like the single-layer planar coil (SLP), but the B1 field slowly becomes weaker farther from the coil unlike the single-layer planar coil (SLP), and accordingly, the double layer surface coil (DLC) maintains greater than or equal to 80% of the strongest B1 field near the center of the examinee.

This double layer surface coil (DLC) may obtain excellent B1 field sensitivity and a deep RF signal permeability depth compared with the single-layer planar coil (SLP) or the single-layer circular coil (SLC), and thus may much improve a signal-to-noise ratio in a magnetic resonance image.

Figure 6:
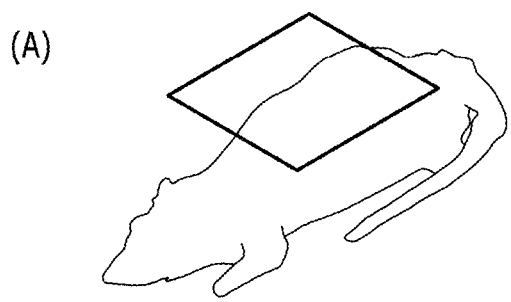
FIG. 6 is perspective views showing each state in which a single-layer planar coil (SLP), a single-layer circular coil (SLC), and a double layer surface coil (DLC) according to an embodiment are respectively mounted on an examinee, which is a mouse.
Figure 6:
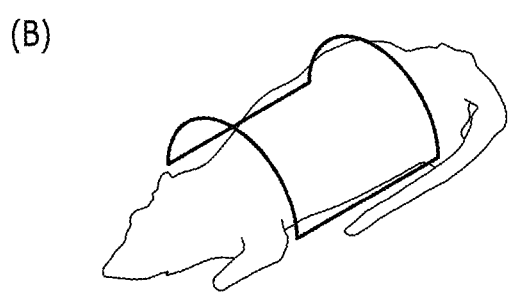
Figure 6:
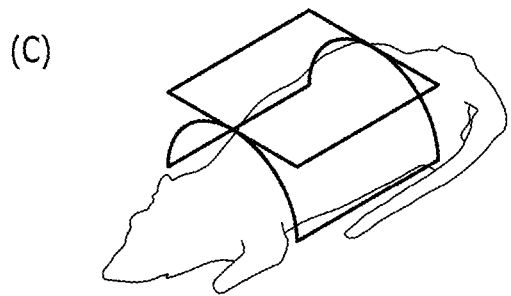
Figure 7:
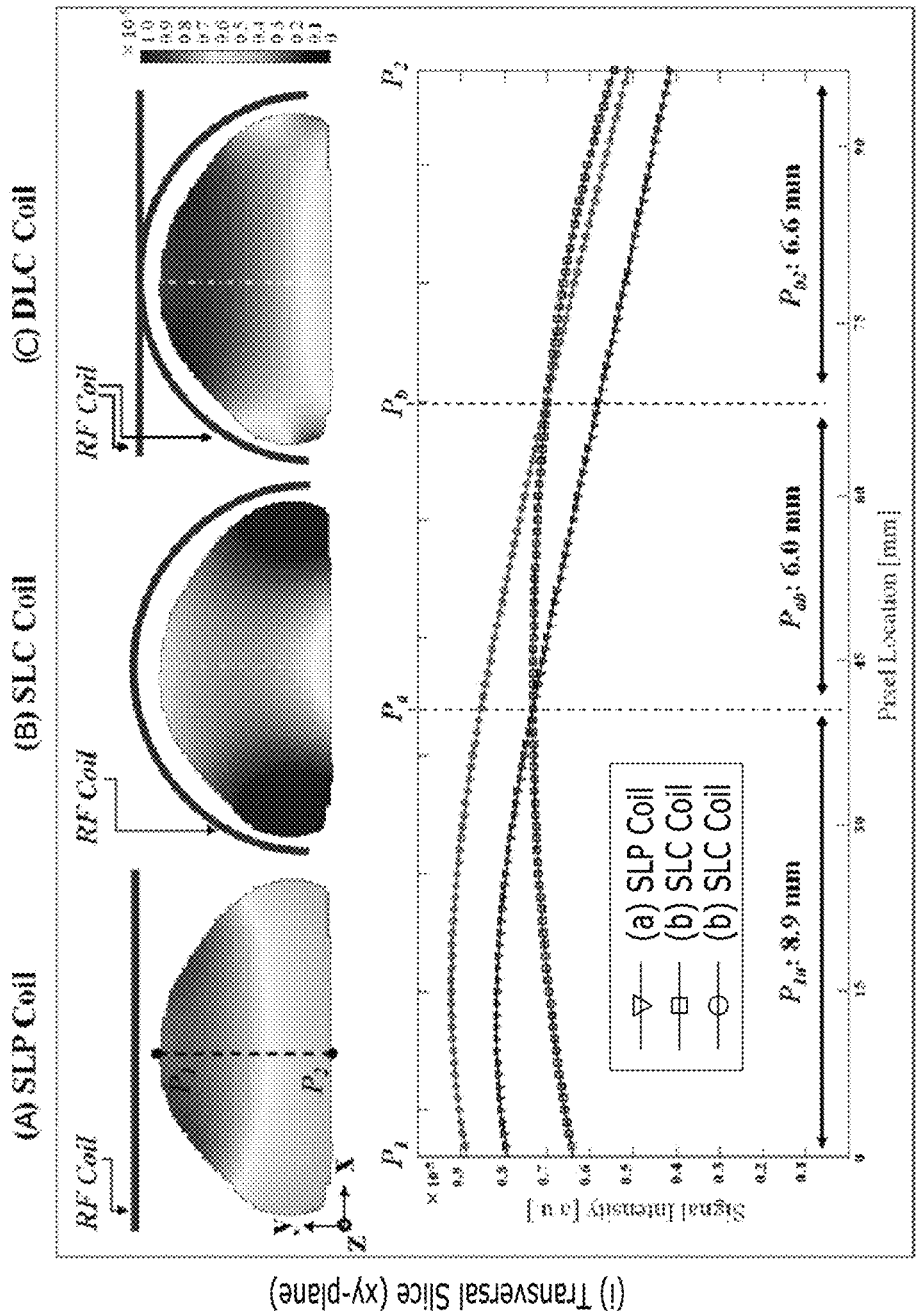
FIG. 7 is a graph showing a magnetic field map measured along the horizontal cross-section of the examinee, which is a mouse on which the surface coils are mounted as shown in FIG. 6, and signal intensity depending on a position.
Figure 8:
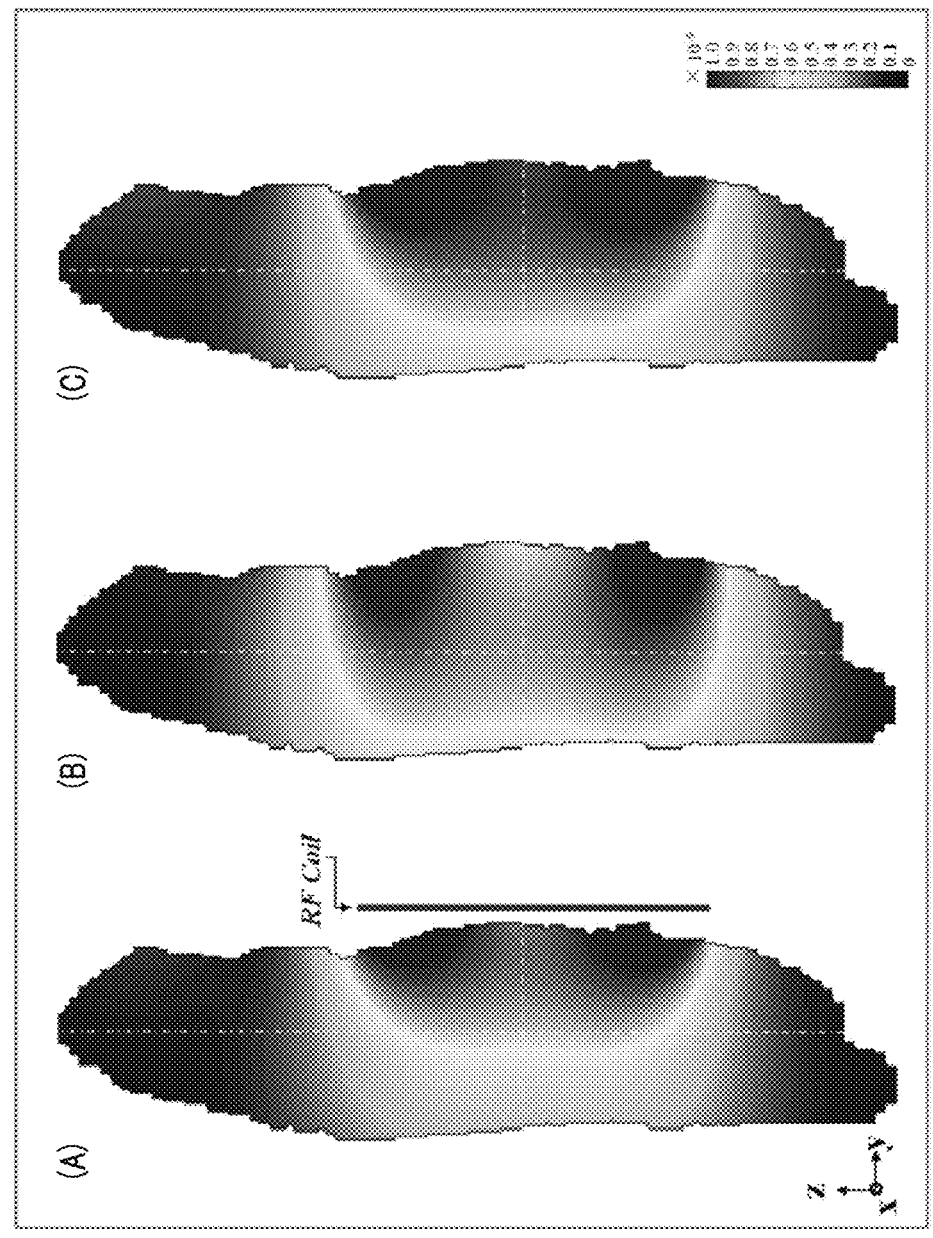
FIG. 8 is a magnetic field map measured along the vertical cross-section of the examinee, which is a mouse on which the surface coils are mounted as shown in FIG. 6.

FIG. 6 is perspective views showing each state in which the single-layer planar coil (SLP), the single-layer circular coil (SLC), and the double layer surface coil (DLC) according to an embodiment are respectively mounted in a mouse as an examinee, FIG. 7 is a graph showing a magnetic field map measured along a horizontal cross-section of the mouse as an examinee on which the surface coil is mounted as shown in FIG. 6 and signal intensity depending on a position, and FIG. 8 is a graph showing a magnetic field map measured along a vertical cross-section of the mouse as an examinee on which the surface coils are mounted as shown in FIG. 6.

In FIG. 6, (A) is a case that the single-layer planar coil (SLP) is mounted on the mouse, (B) is a case that the single-layer circular coil (SLC) is mounted on the mouse, and (C) is a case that the double layer surface coil (DLC) according to an embodiment is mounted on the mouse.

In the signal intensity graph of FIG. 7, a legend "(a) SLP Coil" indicates a case that the single-layer planar coil (SLP) is mounted on a cylindrical examinee, a legend "(b) SLC Coil" indicates a case that a single-layer circular coil (SLC) is mounted on the cylindrical examinee, and a legend "(c) DLC Coil" indicates a case that the double layer surface coil (DLC) according to an embodiment is mounted on the cylindrical examinee.

When a mouse is used as an examinee, similar characteristics to those of the cylindrical examinee may be obtained. In other words, when the double layer surface coil (DLC) according to an embodiment is used, a B1 field is strong at a position close to the surface coil but slowly becomes weaker farther from the coil compared with a single-layer planar coil (SLP), and thus the double layer surface coil (DLC) maintains greater than or equal to 80% of the strongest B1 field near the center of the examinee and thus may image a larger area.

Figure 9:
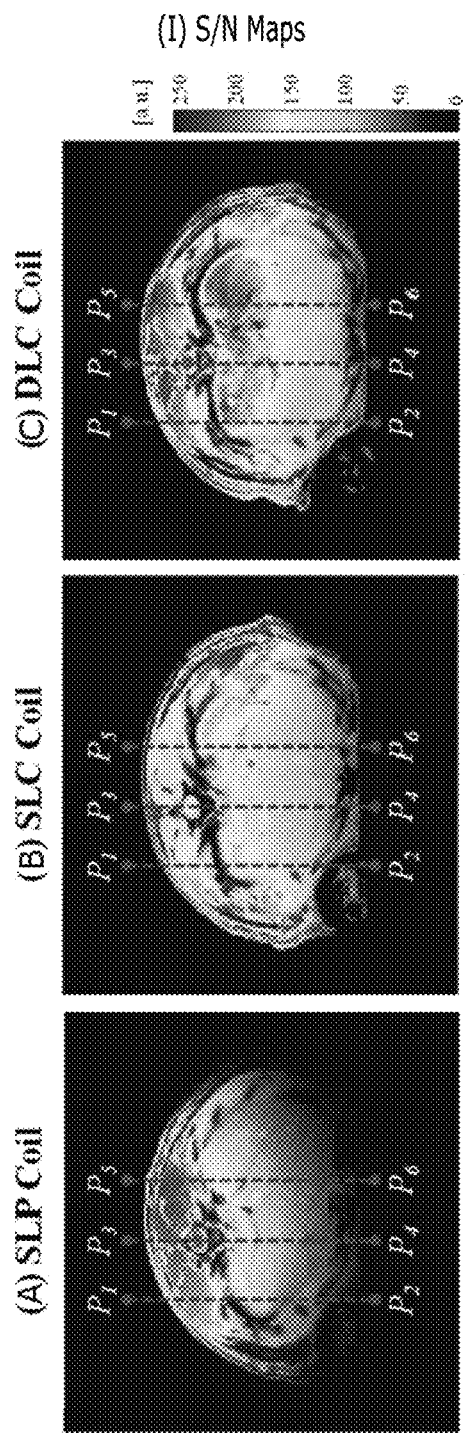
FIG. 9 is a signal-to-noise (S/N) ratio map measured along the horizontal cross-section of the examinee, which is a mouse on which the surface coils are amounted as shown in FIG. 6.

FIG. 9 is a signal-to-noise (S/N) ratio map measured along a horizontal cross-section of a mouse as an examinee on which the surface coils are mounted as shown in FIG. 6, and FIGS. 10, 11, and 12 are graphs showing signal intensity measured along each of P1-P2, P3-P4, and P5 to P6 lines of FIG. 9.

FIG. 9 is a signal-to-noise (S/N) ratio map obtained by using a flash image protocol.

Referring to FIG. 9, a larger area showing a signal-to-noise ratio of greater than or equal to 150 [a.u.] is obtained when the double layer surface coil (DLC) rather than the single-layer planar coil (SLP) or the single-layer circular coil (SLC) is used. Particularly, the double layer surface coil (DLC) according to an embodiment shows a high signal-to-noise ratio in the deepest place of a mouse body (a place where an organ such as the liver and the like is positioned), and thus excellent performance in obtaining a clear image.

Figure 10:
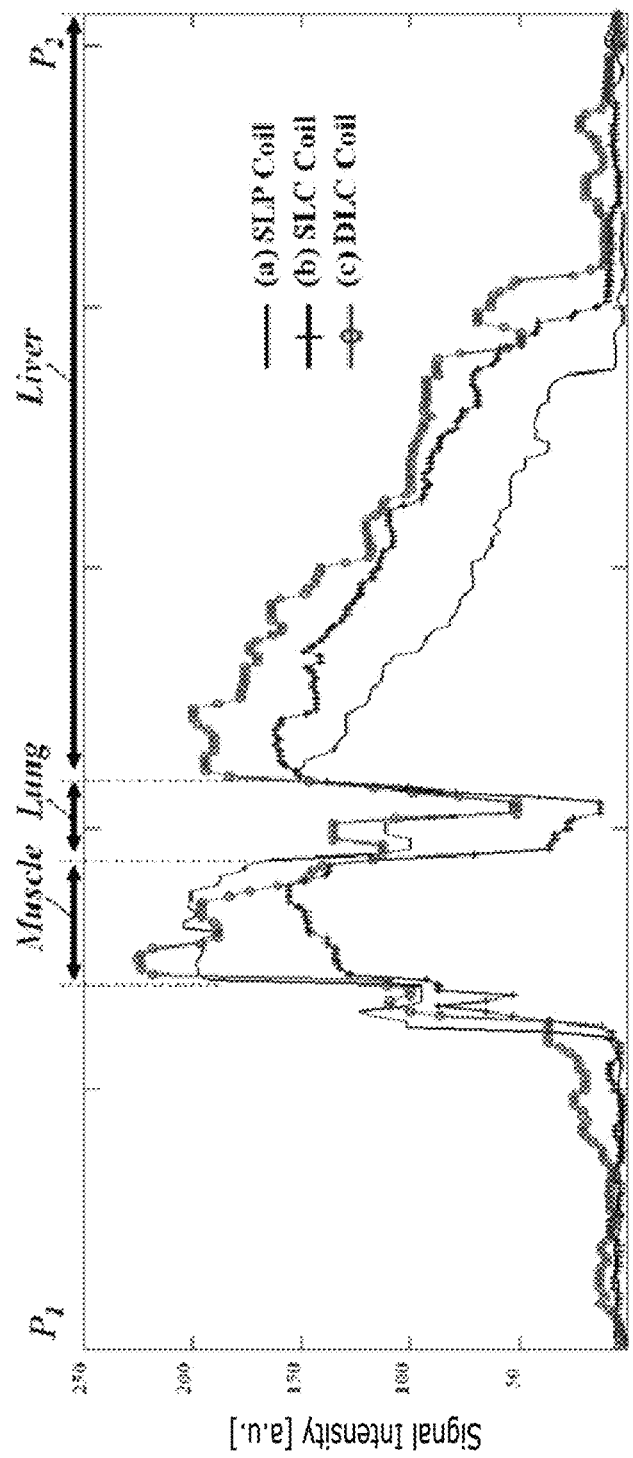
FIGS. 10, 11, and 12 are graphs showing signal intensity measured along each line of P1-P2, P3-P4, and P5-P6 of FIG. 9.
Figure 11:
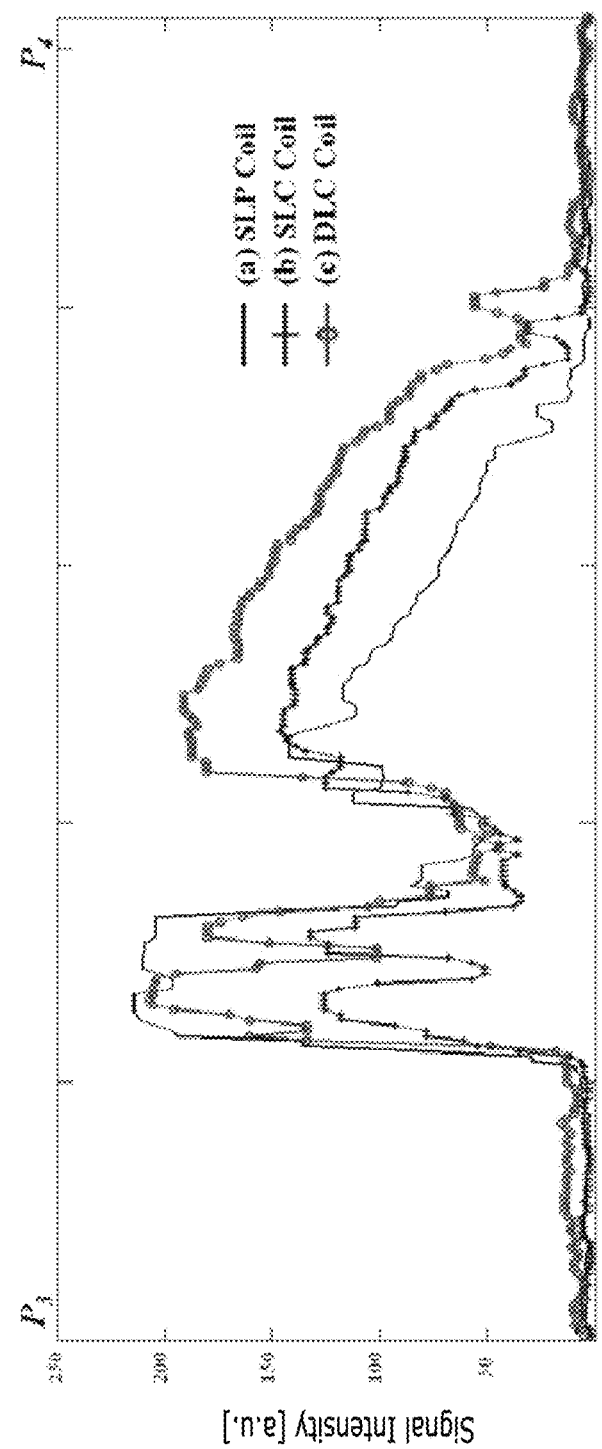
Figure 12:
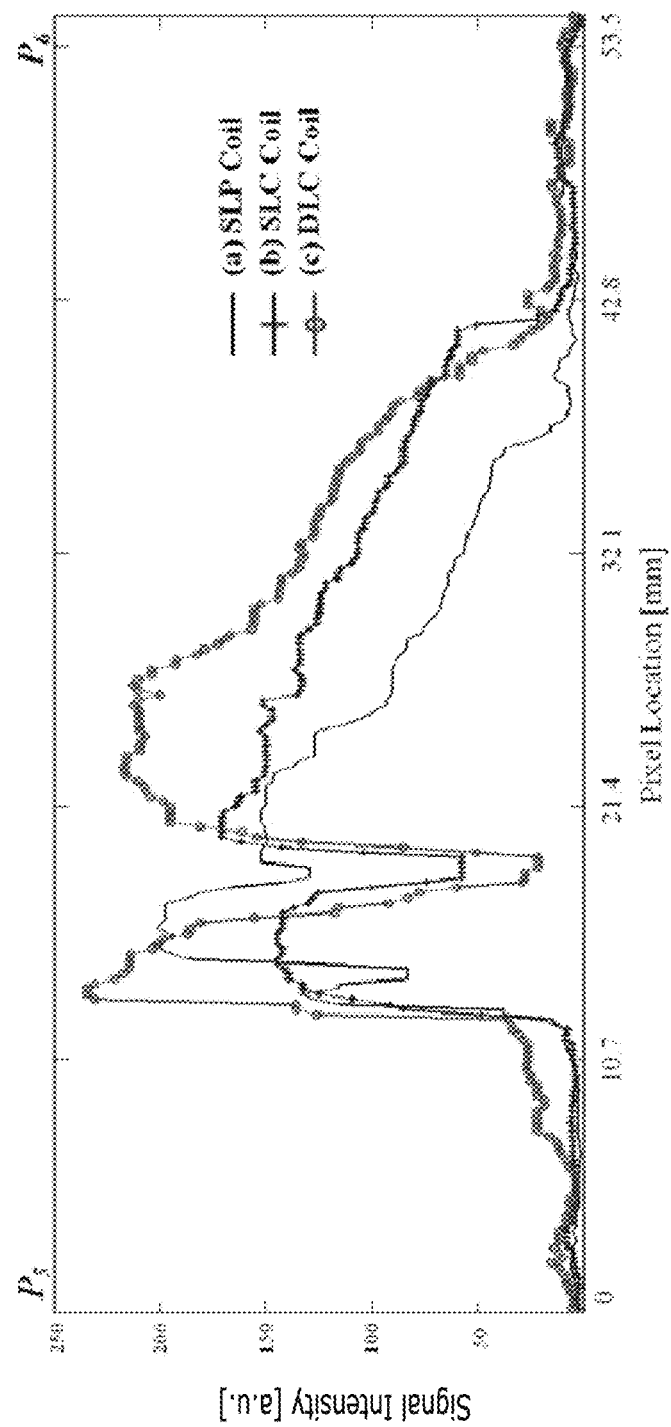

Referring to FIGS. 10 to 12, the double layer surface coil (DLC) may in general show higher signal intensity than the single-layer planar coil (SLP) or the single-layer circular coil (SLC). The single-layer planar coil (SLP) may show a strong signal around the skin (a place where a muscle is mainly positioned) near the coil, but a weaker signal of less than 150 [a.u.] in the center where the liver is positioned and thus may rarely obtain a clear image. The single-layer circular coil (SLC) shows weak signal intensity in both of the skin part and the center part. The double layer surface coil (DLC) shows equivalent signal intensity to that of the single-layer planar coil (SLP) in the skin part and signal intensity of greater than or equal to 150 [a.u.] over a large area in the center. Accordingly, when the double layer surface coil (DLC) according to an embodiment is used, an organ deep in a body as well as the skin area may be clearly imaged.

Figure 13:
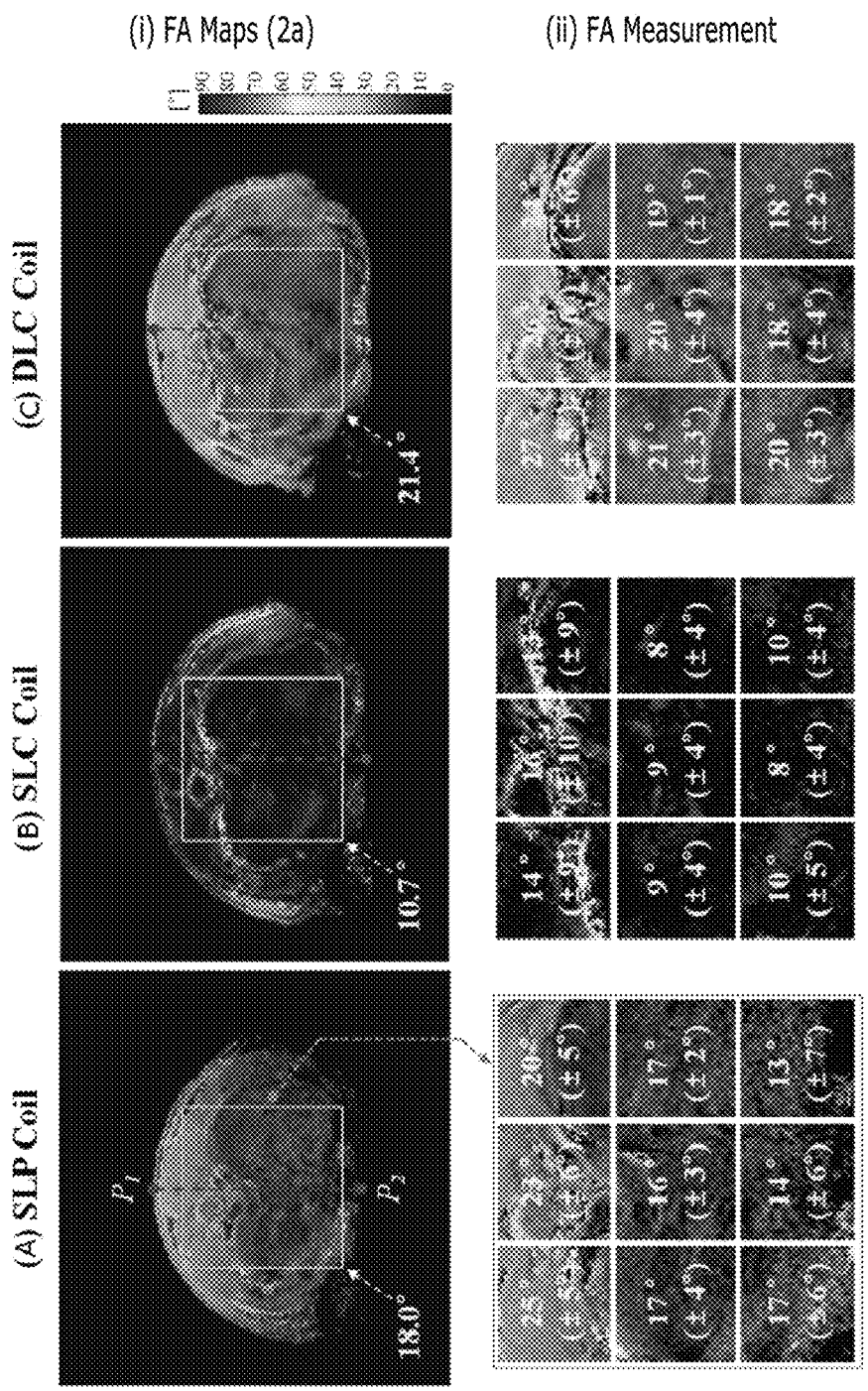
FIG. 13 is a map showing a flipped angle (FA) of a spin of a hydrogen atom which is measured along the horizontal cross-section of the examinee, which is a mouse on which the surface coils are mounted as shown in FIG. 6.
Figure 14:
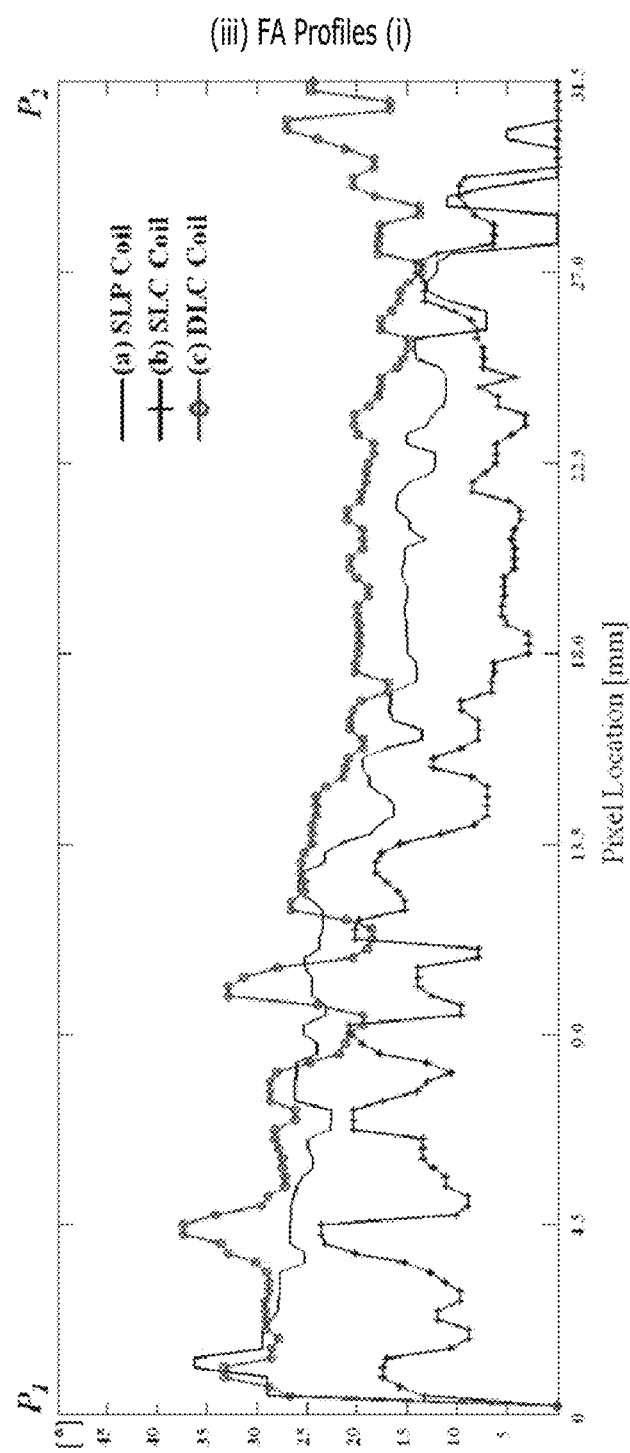
FIG. 14 is a graph showing the flipped angle (FA) of a spin of a hydrogen atom which is measured along P1-P2 (a center line of the cross-section) of FIG. 13.

FIG. 13 is a map showing a flipped angle (FA) of a spin of a hydrogen atom measured along a vertical cross-section of a mouse as an examinee on which surface coils are mounted as shown in FIG. 6, and FIG. 14 is a graph showing a flipped angle (FA) of a spin of a hydrogen atom measured along P1-P2 (a central line of a cross-section) of FIG. 13.

When a RF signal is applied to each coil, its spin is inclined as a hydrogen atom receives energy of water inside the mouse body, and the larger the angle is, the stronger the signal intensity is.

Referring to FIG. 13, a single-layer planar coil (SLP) shows a spin slope of 18° on average in a square area (55 mm×55 mm) partitioned with a white line, a single-layer circular coil (SLC) shows a spin slope of 10.7° on average in the square area (55 mm×55 mm) partitioned with a white line, and a double layer surface coil (DLC) shows a spin slope of 21.4° on average in the square area (55 mm×55 mm) partitioned with a white line. In addition, even in an area (6.6 mm×6.6 mm) obtained by further partitioning the square area (55 mm×55 mm) partitioned with a white line, the double layer surface coil (DLC) shows an average spin slope of greater than or equal to 18° in all the areas, but the single-layer circular coil (SLC) shows an average spin slope of greater than or equal to 18° in no area, and the single-layer planar coil (SLP) shows an average spin slope of greater than or equal to 18° in three out of nine areas.

Referring to FIG. 14, the double layer surface coil (DLC) generally shows a higher spin slope than the single-layer planar coil (SLP) or the single-layer circular coil (SLC).

In this way, the double layer surface coil (DLC) according to an embodiment may bring about excellent B1 field sensitivity and a deep RF signal permeability depth compared with the single-layer planar coil (SLP) or the single-layer circular coil (SLC), and accordingly, an image with high quality may be obtained by much improving a signal-to-noise ratio in a magnetic resonance image.

Figure 15:
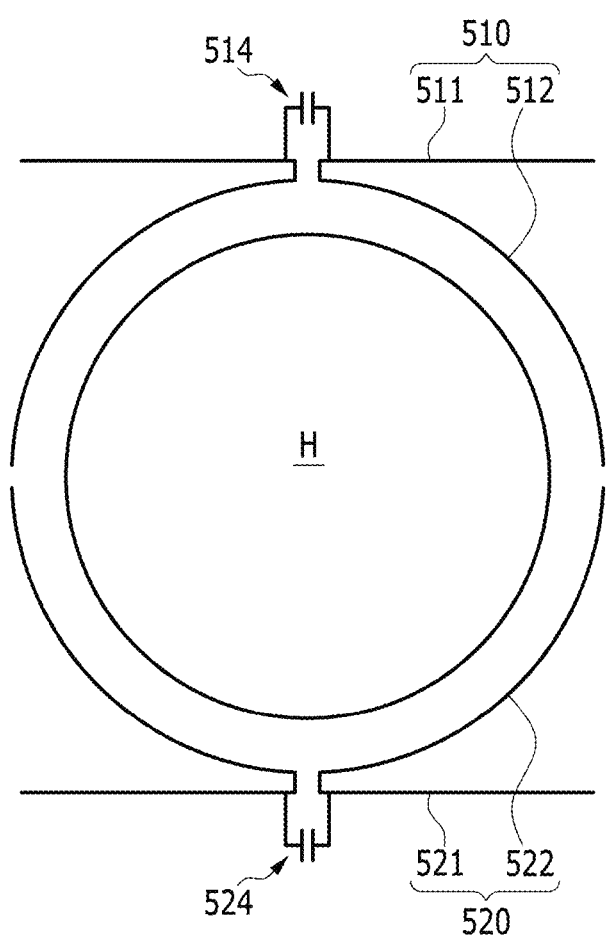
FIG. 15 is a side view showing a surface coil for a magnetic resonance imaging system according to another embodiment.

FIG. 15 is a side view showing the surface coil for a magnetic resonance imaging system according to another embodiment.

In FIG. 15, two surface coils of embodiment of FIG. 2 are disposed to face each other with an examinee (H) in the middle. In other words, a first double layer coil 510 including a first plane coil unit 511 and a first curved surface coil unit 512 and a second double layer coil 520 including a second plane coil unit 521 and a second curved surface coil unit 522 are symmetrically disposed with the examinee (H) in the middle to form two channels. The first double layer coil 510 and the second double layer coil 520 respectively include capacitors 514 and 524. The capacitors 514 and 524 may be used in various numbers and positions as shown in FIG. 2.

Figure 16:
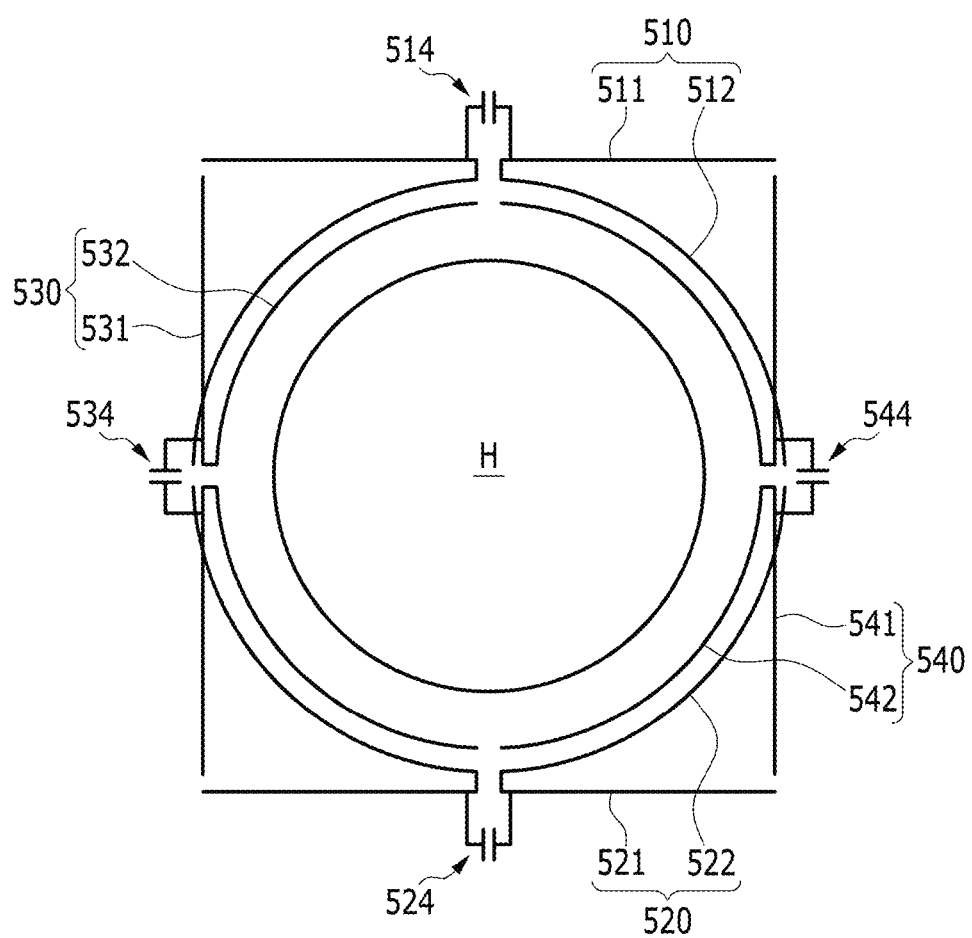
FIG. 16 is a side view showing a surface coil for a magnetic resonance imaging system according to still another embodiment.

In addition, FIG. 16 is a side view showing the surface coil for a magnetic resonance imaging system according to another embodiment.

The embodiment of FIG. 16 has a structure in which four surface coils according to the embodiment of FIG. 2 are disposed to face each other at the left and right and up and down with an examinee (H) in the center. In other words, the first double layer coil 510 including the first plane coil unit 511 and the first curved surface coil unit 512 and the second double layer coil 520 including the second plane coil unit 521 and the second curved surface coil unit 522 are symmetrically disposed up and down with the examinee (H) in the center, and a third double layer coil 530 including a third plane coil unit 531 and a third curved surface coil unit 532 and a fourth double layer coil 540 including a fourth plane coil unit 541 and a fourth curved surface coil unit 542 are symmetrically disposed left and right with the examinee (H) in the center to form 4 channels. Circular arc parts of the first curved surface coil unit 512, the second curved surface coil unit 522, the third curved surface coil unit 532, and the fourth curved surface coil unit 542 are all disposed on the cylindrical surface of the same axis. The first plane coil unit 511 and the second plane coil unit 521 are disposed on each plane parallel to each other, the third plane coil unit 531 and the fourth plane coil unit 541 are disposed on each plane parallel to each other, and the first plane coil unit 511 is disposed on the plane perpendicularly crossing a plane on which the third plane coil unit 531 is disposed.

The first double layer coil 510, the second double layer coil 520, the third double layer coil 530, and the fourth double layer coil 540 respectively include capacitors 514, 524, 534, and 544. A position and number of the capacitors 514, 524, 534, and 544 may be variously changed as illustrated with reference to FIG. 2.

Figure 17:
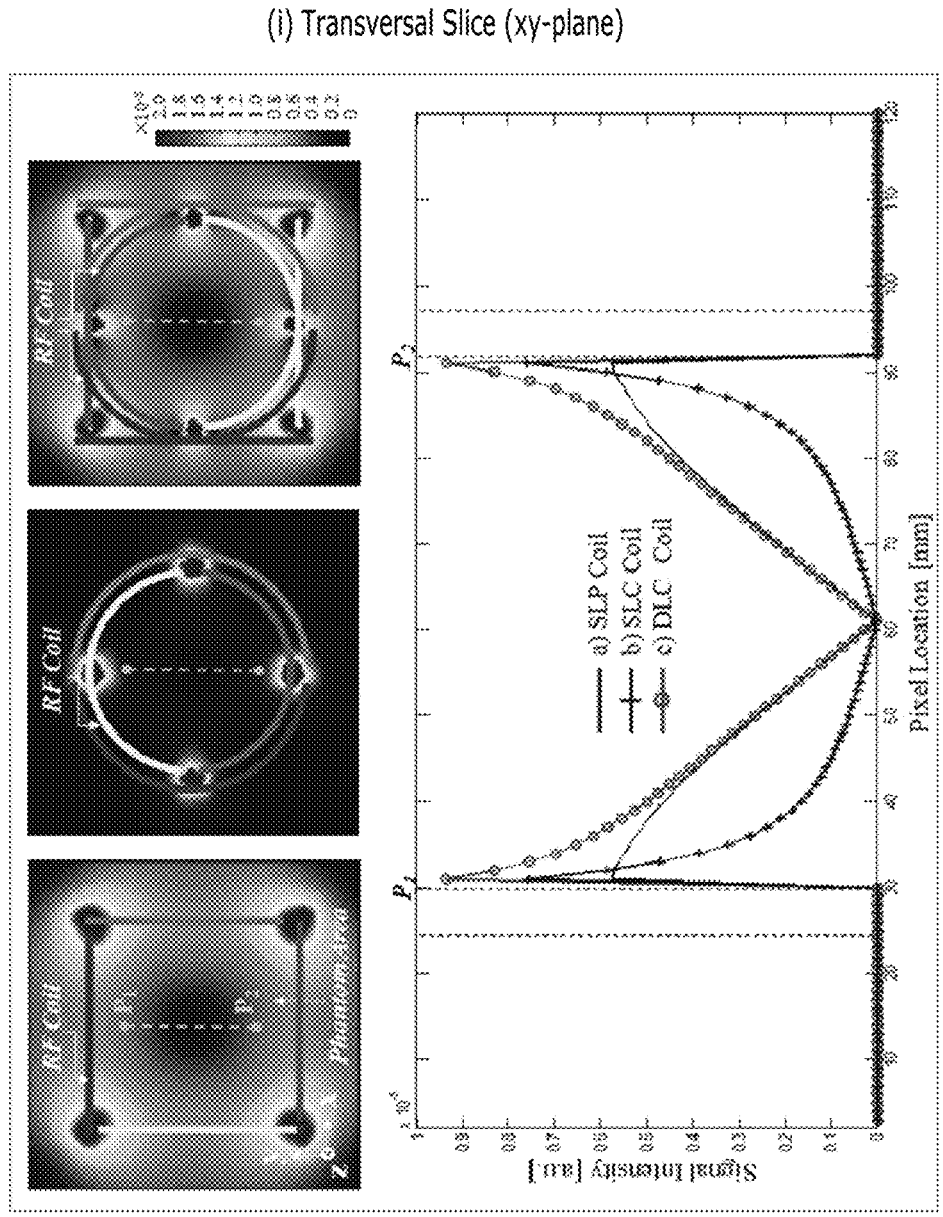
FIG. 17 is a graph showing a magnetic field map measured along the horizontal surface of an examinee and signal intensity depending on a place in each case that four single-layer planar coils (SLP) are disposed in four sides of a cylindrical examinee, that four single-layer circular coils (SLC) are disposed in four sides of the cylindrical examinee, and that double layer surface coils (DLC) are disposed in four sides of the cylindrical examinee.

FIG. 17 is a graph showing each magnetic field map and signal intensity depending on a position regarding each case in which 4 single-layer planar coils (SLP) are disposed at four sides of a cylindrical examinee, in which 4 single-layer circular coils (SLC) are disposed at four sides of the cylindrical examinee, and in which the double layer surface coil (DLC) is disposed at four sides of the cylindrical examinee as shown in FIG. 16.

Referring to FIG. 17, a B1 field shows strong intensity in all areas of the examinee when the double layer surface coil (DLC) is disposed to form 4 channels compared to when the single-layer planar coil (SLP) or the single-layer circular coil (SLC) is disposed to form the 4 channels.

In this way, the surface coil for a magnetic resonance imaging system according to an embodiment may be used as a single channel or multiple channels. The aforementioned embodiments exemplify 2 channels and 4 channels, but may include 3 channels or greater than or equal to 5 channels.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A surface coil for a magnetic resonance imaging system, comprising:
    a first plane coil disposed on a first plane; and
    a first curved surface coil disposed symmetrically and tangentially to the first plane coil, and configured to receive an examinee into a cavity formed within a curve of the first curved surface coil,
    wherein the first plane coil and the first curved surface coil form a single closed loop, and
    wherein the first plane coil and the first curved surface coil are electrically connected to each other through at least two surface portions to form a resonance circuit.

2. The surface coil of claim 1, further comprising a first capacitor connected to any one or any combination of the first plane coil and the first curved surface coil.

3. The surface coil of claim 2, wherein the first capacitor is disposed at a connecting location where the first curved surface coil is connected to the first plane coil.

4. The surface coil of claim 3, wherein the first plane coil is severed to have both ends in the connecting location, the first curved surface coil is severed to have both ends in the connecting location, and the first capacitor disposed at the connecting location connects between both severed ends of the first plane coil and between both severed ends of the first curved surface coil.

5. The surface coil of claim 1, wherein the first plane coil has a quadrilateral shape, and the first curved surface coil has a parabolic cylinder shape.

6. The surface coil of claim 5, wherein the first plane coil and the first curved surface coil are respectively severed to have both ends at the tangent, and both of the severed ends of the first plane coil are respectively connected to both of the severed ends of the first curved face coil.

7. The surface coil of claim 6, wherein a first capacitor connects both of the severed ends of the first plane coil and the first curved surface coil.

8. The surface coil of claim 7, further comprising: a second capacitor respectively inserted in each of opposing straight sides of the first curved surface coil.

9. The surface coil of claim 1, further comprising a second plane coil disposed on second plane, and
    a second curved surface coil having a parabolic cylinder shape and disposed symmetrically to the second plane coil, and the second plane coil disposed tangentially to the second curved surface coil,
    wherein the second plane coil and the second curved surface coil are electrically connected to each other through at least two surface portions.

10. The surface coil of claim 9, wherein the first plane coil is disposed to face the second plane coil in parallel, and the first curved surface coil and the second curved surface coil are disposed around a cylindrical axis.

11. The surface coil of claim 10, wherein a first capacitor connected to any one or any combination of the first plane coil and the first curved surface coil, and a second capacitor connected to any one or any combination of the second plane coil and the second curved surface coil.

12. The surface coil of claim 9, wherein the surface coil further comprises a third plane coil disposed on third plane, and a third curved surface coil having a parabolic cylinder shape and disposed symmetrically to the third plane coil, and the third plane coil disposed tangentially to the third curved surface coil, wherein the third plane coil and the third curved surface coil are electrically connected to each other through at least two surface portions.

13. The surface coil of claim 12, wherein the surface coil further comprises a fourth plane coil disposed on fourth plane, and a fourth curved surface coil having a parabolic cylinder shape and disposed symmetrically to the fourth plane coil, and the fourth plane coil disposed tangentially to the fourth curved surface coil, wherein the fourth plane coil and the fourth curved surface coil are electrically connected to each other through two surface portions.

14. The surface coil of claim 13, wherein the third plane coil and the fourth plane coil are disposed to face each other in parallel, and the third curved surface coil and the fourth curved surface coil are disposed around the cylindrical axis.

15. The surface coil of claim 14, wherein the first plane and the third plane are perpendicular each to the other.

16. The surface coil of claim 15, further comprising:

a first capacitor connected to any one or any combination of the first plane coil and the first curved surface coil, a second capacitor connected to any one or any combination of the second plane coil and the second curved surface coil, a third capacitor connected to any one or any combination of the third plane coil and the third curved surface coil, and a fourth capacitor connected to any one or any combination of the fourth plane coil and the fourth curved surface coil.

17. A magnetic resonance imaging system comprising the surface coil of claim 1.

18. The magnetic resonance imaging system of claim 17, further comprising: a first capacitor connected to any one or any combination of the first plane coil and the first curved surface coil.

19. The magnetic resonance imaging system of claim 18, wherein the first capacitor is disposed at a connecting position where the first curved surface coil and the first plane coil are connected to each other.

20. The magnetic resonance imaging system of claim 19, wherein the first plane coil is severed to have both ends at the connecting position, the first curved surface coil is severed to have both ends at the connecting position, and the capacitors disposed on the connecting positions are connected to both of the severed ends of the first plane coil and both of the severed ends of the first curved surface coil.

* * * * *